United States Patent [19]
Amschler

[11] Patent Number: 5,376,656
[45] Date of Patent: Dec. 27, 1994

[54] ARYLPYRIDAZINONES

[75] Inventor: Hermann Amschler, Radolfzell, Germany

[73] Assignee: BYK Gulden Lomberg Chemische Fabrik GmbH, Constance, Germany

[21] Appl. No.: 39,132

[22] PCT Filed: Oct. 12, 1991

[86] PCT No.: PCT/EP91/01942

§ 371 Date: Apr. 16, 1993

§ 102(e) Date: Apr. 16, 1993

[87] PCT Pub. No.: WO92/06963

PCT Pub. Date: Apr. 30, 1992

[22] Filed: Apr. 16, 1993

[30] Foreign Application Priority Data

Oct. 16, 1990 [CH] Switzerland ............ 03306/90

[51] Int. Cl.⁵ .................. C07D 237/14; A61K 31/50
[52] U.S. Cl. ...................................... 514/247; 544/239
[58] Field of Search ...................... 544/239; 514/247

[56] References Cited

U.S. PATENT DOCUMENTS

| | | | |
|---|---|---|---|
| 4,088,762 | 5/1978 | Hakim et al. | 544/239 |
| 4,665,074 | 5/1987 | Amschler | 514/247 |
| 4,707,481 | 11/1987 | Amschler et al. | 514/247 |
| 5,236,918 | 8/1993 | Amschler et al. | 544/239 |

Primary Examiner—Emily Bernhardt
Attorney, Agent, or Firm—Jacobson, Price, Holman & Stern

[57] ABSTRACT

6-Aryl-3[2H]pyridazinones of formula I

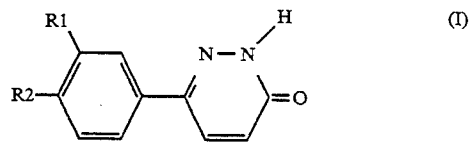

wherein one of the substituents R1 and R2 denotes methoxy, difluoromethoxy or ethoxy, and the other denotes C4–C7-cycloalkoxy or C3–C7-cycloaklylmethoxy, and their salts with bases, and medicaments compounded therefrom are useful for treating inflammatory and allergen-induced bronchial diseases.

7 Claims, No Drawings

ARYLPYRIDAZINONES

TECHNICAL FIELD

The invention relates to 6-aryl-3[2H]pyridazinones, their preparation and use and medicaments containing them.

PRIOR ART

From European patent 163 965 certain pyridazinones are known which have bronchospasmolytic and/or cardiotonic activity.

DESCRIPTION OF THE INVENTION

It has been found that the 6-aryl-3[2H]pyridazinones described below have advantageous pharmcological properties by which they differ surprisingly from the compounds of European patent 163 965.

The invention relates to 6-aryl-3[2H]pyridazinones of the general formula I

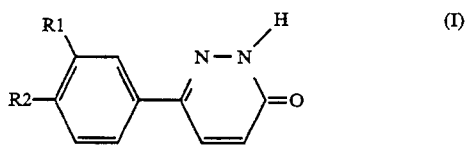

wherein one of the substituents R1 and R2 denotes methoxy, difluoromethoxy or ethoxy and the other denotes C4–C7-cycloalkoxy or C3–C7-cycloalkylmethoxy, and their salts with bases.

C4–C7-Cycloalkoxy represents, for example, cyclobutyloxy, cyclopentyloxy, cyclohexyloxy and cycloheptyloxy, cyclopentyloxy being preferred.

C3–C7-Cycloalkylmethoxy represents, for example, cyclopropylmethoxy, cyclobutylmethoxy, cyclopentylmethoxy, cyclohexylmethoxy and cycloheptylmethoxy, cyclopropylmethoxy and cyclobutylmethoxy being preferred.

Possible salts are salts with inorganic and organic bases. The pharmacologically tolerated salts of the inorganic and organic bases usually used in galenics may be mentioned in particular. Salts which are not pharmacologically tolerated and may initially be obtained as process products, for example, in the preparation of the compounds according to the invention on an industrial scale are converted into pharmacologically tolerated salts by processes known to the expert. Examples of such suitable salts are water-soluble and water-insoluble salts with bases, the cations of the alkali metals or alkaline earth metals being used above all as the cations for the salt formation; however, it is also possible to use the corresponding cations of organic nitrogen bases, such as amines or amino-alkanols, aminosugars, etc. Salts which may be mentioned as examples are those of sodium, magnesium, calcium, dimethylamine, diethylamine, ethanolamine, diethanolamine, triethanolamine, glucamine, N-methylglucamine (meglumine), glucosamine and N-methylglucosamine.

One embodiment (embodiment a) of the invention comprises 6-aryl-3[2H]pyridazinones of the abovementioned general formula I, wherein R1 denotes methoxy, difluoromethoxy or ethoxy, R2 denotes C4–C6-cycloalkoxy or C3–C6-cycloalkylmethoxy, and their salts with bases.

A further embodiment (embodiment b) of the invention comprises 6-aryl3μH]pyridazinones of the above-mentioned general formula I, wherein R1 denotes C4–C6-cycloalkoxy or C3–C6-cycloalkylmethoxy and R2 denotes methoxy, difluoromethoxy or ethoxy, and their salts with bases.

Embodiment b is preferable to embodiment a.

Preferred compounds according to the invention are those of the formula I, wherein one of the substituents R1 and R2 denotes cyclopentyloxy, cycloheptyloxy, cyclopropylmethoxy or cyclobutylmethoxy, and the other denotes methoxy or difluoromethoxy, and their pharmacologically tolerated salts with bases.

The invention furthermore relates to the use of the compounds according to the invention in the treatment or prophylaxis of illnesses based on a disease of the bronchi.

The invention furthermore relates to the use of the compounds according to the invention and their pharmacologically tolerated salts for the preparation of medicaments for the treatment and/or prophylaxis of diseases of the bronchi.

The invention furthermore relates to a process for the preparation of the 6-aryl-3[2H]pyridazinones of the general formula I and of their salts with bases, which comprises a) oxidizing a 6-aryltetrahydropyridazinone of the general formula II

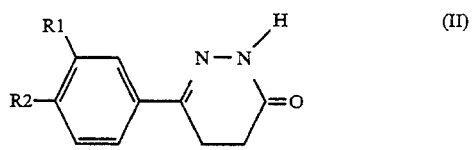

in which R1 and R2 have the abovementioned meaning, and, if desired, then converting the resulting pyridazinone into a salt, or b) reacting a morpholinobutyric acid of the general formula III

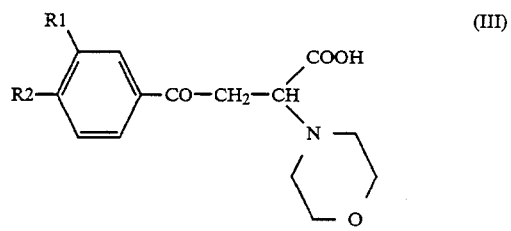

in which R1 and R2 have the abovementioned meaning, with hydrazine and, if desired, then converting the resulting pyridazinone into a salt, or c) reacting an acrylic acid of the general formula IV

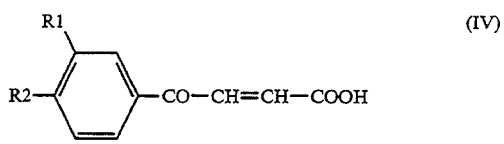

in which R1 and R2 have the abovementioned meaning, with hydrazine and, if desired, then converting the resulting pyridazinone into a salt.

The process according to the variant a), b) or c) is carried out by methods as described, e.g., in European patent 163 965. The process is carried out preferably according to variant c).

The starting compounds of the formulae II, III and IV are known, or they can be prepared by known processes, such as are described, e.g., in European patent 163 965.

The following examples serve to illustrate the invention in more detail. m.p. denotes melting point, h denotes hour(s).

EXAMPLES 6-(3-Cyclopropylmethoxy-4-difluoromethoxyphenyl)-3[2H]pyridazinone 22 g of 3-cyclopropylmethoxy-4-difluoromethoxy-acetophenone are added at room temperature to a solution of 15.8 g of glyoxylic acid monohydrate in 15 ml of dioxan. The mixture is heated under a nitrogen atmosphere to 100° C. for 3 h with vigorous stirring, and then cooled in an ice bath. 13 ml of a concentrated aqueous ammonia solution are added dropwise with ice cooling in such a manner that the inner temperature does not exceed 40° C. After addition of 8.6 g of hydrazine hydrate to the acrylic acid formed in situ, the mixture is heated for 1 h at 80° C. After cooling and addition of 200 ml of water and 200 ml of a saturated ammonium chloride solution, the mixture is extracted three times with ethyl acetate. The combined organic phases are dried over magnesium sulfate and concentrated. The obtained crude product is purified over a silica gel column (solvent: acetonitrile/ammonia 9:1) and crystallised from ethyl acetate. 18.3 g (69 %) of the title compound with m.p. 141.5° C. are obtained.

The following pyridazinones are obtained analogously:

6-(4-Cyclopropylmethoxy-3-difluoromethoxyphenyl)-3[2H]pyridazinone, m.p. 172° C.

6-(3-Cyclopentyloxy-4-methoxyphenyl)-3[2H]pyridazinone, m.p. 201° C.

6-(3-Cycloheptyloxy-4-methoxyphenyl)-3[2H]pyridazinone, m.p. 172° C.

6-(3-Cyclobutylmethoxy-4-methoxyphenyl)-3[2H]pyridazinone, m.p. 2010° C.

6-(3-Cycloheptyloxy-4-difluoromethoxyphenyl)-3[2H]pyridazinone, m.p. 139°-140° C.

6-(3-Cyclopentyloxy-4-difluoromethoxyphenyl)-3[2H]pyridazinone, m.p. 113° C.

COMMERCIAL USEFULNESS

The 6-aryl-3[2H]pyridazinones according to the invention have valuable pharmacological properties which render them commercially usable. They are distinguished above all by those properties which suggest they are suitable for the therapy of diseases of the respiratory tract of various origins. In particular, inflammatory and allergen-induced bronchial diseases can be treated on the basis of the antiinflammatory and broncholytic activity of the compounds according to the invention, the comparatively surprising strong antiinflammatory activity of the compounds according to the invention being stressed in particular. In addition, the compounds according to the invention are distinguished by a low toxicity, a wide therapeutic range and the absence of substantial side effects.

The broncholytic and antiinflammatory activity of the 6-aryl-3[2H]pyridazinones enables them to be used in human and veterinary medicine, in which they are used for the treatment and prophylaxis of illnesses based on diseases of the bronchi. For example, acute and chronic obstructive diseases of the respiratory tract of various origins (bronchitis, allergic bronchitis, bronchial asthma) in humans and animals can be treated.

The invention thus furthermore relates to a process for the treatment of mammals, including humans, suffering from one of the abovementioned diseases. The process is characterized in that a therapeutically active and pharmacologically tolerated amount of one or more of the compounds according to the invention is administered to the sick mammal.

The invention furthermore relates to the compounds according to the invention for use in the treatment and-/or prophylaxis of illnesses based on diseases of the bronchi.

The invention similarly relates to the use of the compounds according to the invention for the preparation of medicaments which are employed for the treatment and/or prophylaxis of illnesses based on diseases of the bronchi. The invention furthermore relates to medicaments for the treatment and/or prophylaxis of illnesses based on diseases of the bronchi, which contain one or more of the compounds according to the invention and/or their pharmacologically tolerated salts.

The medicaments according to the invention are prepared by processes which are known per se, reference being made, for example, to the statements in European Patent 163 965 in respect of the formulations, dosages, presentation forms, etc.

I claim:

1. A 6-aryl-3[2H]pyridazinone of formula I

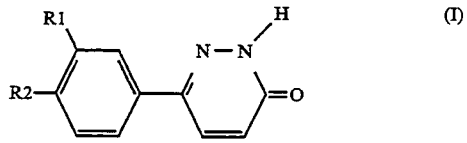

wherein one of the substituents R1 and R2 denotes methoxy, difluoromethoxy or ethoxy and the other denotes C4–C7-cycloalkoxy or C3–C7-cycloalkylmethoxy, or a salt thereof with a base.

2. A compounds of formula I according to claim 1, wherein R1 denotes methoxy, difluoromethoxy or ethoxy, R2 denotes C4–C6-cycloalkoxy or C3–C6-cycloalkylmethoxy, or a salt thereof with a base.

3. A compounds of formula I according to claim 1, wherein R1 denotes C4–C6-cycloalkoxy or C3–C6-cycloalkylmethoxy and R2 denotes methoxy, difluoromethoxy or ethoxy, or a salt thereof with a with base.

4. A compounds of formula I according to claim 1, wherein one of the substituents R1 and R2 denotes cyclopentyloxy, cycloheptyloxy, cyclopropylmethoxy or cyclobutylmethoxy, and the other denotes methoxy or difluoromethoxy, or a pharmacologically tolerated salt with base.

5. A broncholytic and antiinflammatory medicament composition comprising a pharmaceutically-acceptable carrier and an effective amount of a compound of claim 1 or of a pharmacologically-tolerated salt thereof.

6. A method which comprises administering an effective amount of an active compound having broncholytic and/or antiinflammatory activity to a mammal in need of such treatment, wherein the compound is a compound of claim 1 or a pharmacologically-tolerated salt thereof.

7. A method which comprises administering an effective amount of an active compound to a mammal afflicted with or subject to a disease of the bronchi, wherein the active compound is a compound of claim 1 or a pharmacologically-tolerated salt thereof.

* * * * *